(12) United States Patent
Simard et al.

(10) Patent No.: US 6,576,248 B1
(45) Date of Patent: Jun. 10, 2003

(54) PIGMENTED VITAMIN C COMPOSITION

(75) Inventors: Claude Simard, Sparrowbush, NY (US); Ernest S. Curtis, Milford, PA (US); Harold E. Pahlck, Waldwick, NJ (US)

(73) Assignee: Avon Products, Inc., New York, NY (US)

( * ) Notice: Subject to any disclaimer, the term of this patent is extended or adjusted under 35 U.S.C. 154(b) by 55 days.

(21) Appl. No.: 09/659,223

(22) Filed: Sep. 11, 2000

Related U.S. Application Data

(63) Continuation-in-part of application No. 09/150,806, filed on Sep. 10, 1998, now Pat. No. 6,299,889.

(51) Int. Cl.[7] .............................. A61K 7/00; A61K 7/42; A61K 31/34
(52) U.S. Cl. .................. 424/401; 424/59; 514/474; 514/937; 514/939
(58) Field of Search .................. 424/401, 59; 514/474, 514/937, 939

(56) References Cited

U.S. PATENT DOCUMENTS

| | | | |
|---|---|---|---|
| 3,958,017 A | 5/1976 | Morse et al. | 426/72 |
| 4,518,614 A | 5/1985 | Parkinson | 514/2 |
| 4,692,339 A | 9/1987 | Stetson et al. | 426/72 |
| 4,695,452 A | 9/1987 | Gannis et al. | 424/59 |
| 4,704,280 A | 11/1987 | Bates | 424/195.1 |
| 4,818,521 A | 4/1989 | Tamabuchi | 424/62 |
| 4,822,816 A | 4/1989 | Markham | 514/474 |
| 4,885,157 A | 12/1989 | Fiaschetti | 424/59 |
| 4,983,382 A | 1/1991 | Wilmott et al. | 424/62 |
| 5,087,446 A | 2/1992 | Suzuki et al. | 424/62 |
| 5,140,043 A | 8/1992 | Darr et al. | 514/474 |
| 5,141,758 A | 8/1992 | Monte | 426/72 |
| 5,151,476 A | 9/1992 | Marshall et al. | 526/93 |
| 5,204,105 A | 4/1993 | Mausner | 424/401 |
| 5,208,028 A | 5/1993 | Clement et al. | 424/401 |
| 5,215,759 A | 6/1993 | Mausner | 424/489 |
| 5,229,147 A | 7/1993 | Kubota et al. | 426/2 |
| 5,230,836 A | 7/1993 | Todd, Jr. | 252/407 |
| 5,230,916 A | 7/1993 | Chang et al. | 426/330.6 |
| 5,258,179 A | 11/1993 | Bracco et al. | 424/94.1 |
| 5,290,481 A | 3/1994 | Todd, Jr. | 252/407 |
| 5,296,249 A | 3/1994 | Todd, Jr. | 426/541 |
| 5,308,621 A | 5/1994 | Taylor et al. | 424/401 |
| 5,314,686 A | 5/1994 | Todd, Jr. | 424/401 |
| 5,425,939 A | 6/1995 | Guerrero et al. | 424/78.02 |
| 5,492,935 A | 2/1996 | Yu et al. | 514/703 |
| 5,508,022 A | 4/1996 | Clement et al. | 424/43 |
| 5,520,991 A | 5/1996 | Eustatiu | 424/195.1 |
| 5,531,993 A | 7/1996 | Griat | 424/401 |
| 5,536,500 A | 7/1996 | Galey et al. | 424/401 |
| 5,552,446 A | 9/1996 | Candau et al. | 514/772.4 |
| 5,560,917 A | 10/1996 | Cohen et al. | 424/401 |
| 5,574,063 A | 11/1996 | Perricone | 514/474 |
| 5,609,875 A | 3/1997 | Hadas | 424/195.1 |
| 5,616,332 A | 4/1997 | Herstein | 424/401 |
| 5,629,004 A | 5/1997 | Candau et al. | 424/401 |
| 5,658,580 A | 8/1997 | Mausner | 424/401 |
| 5,660,839 A | 8/1997 | Allec et al. | 424/401 |
| 5,681,554 A | 10/1997 | Cannell et al. | 424/70.14 |
| 5,702,688 A | 12/1997 | Yu et al. | 424/59 |
| 5,703,122 A | 12/1997 | Duffy | 514/474 |
| 5,733,572 A | 3/1998 | Unger et al. | 424/450 |
| 5,736,567 A | 4/1998 | Cantin et al. | 514/474 |
| 5,738,839 A | 4/1998 | Clement et al. | 424/43 |
| 5,750,123 A | 5/1998 | Znaiden et al. | 424/401 |
| 5,780,060 A | 7/1998 | Levy et al. | 424/489 |
| 5,801,192 A | 9/1998 | Dumas et al. | 514/474 |
| 5,827,520 A | 10/1998 | de Salvert | 424/401 |
| 5,846,996 A | 12/1998 | Fallick | 514/474 |
| 5,853,741 A | 12/1998 | Znaiden et al. | 424/401 |
| 5,866,106 A | 2/1999 | Papay | 424/61 |
| 5,871,759 A | 2/1999 | Hamano et al. | 424/401 |
| 5,902,591 A | * 5/1999 | Herstein | 424/401 |
| 5,976,510 A | * 11/1999 | Cernasov et al. | 424/400 |
| 5,997,887 A | * 12/1999 | Ha et al. | 424/401 |
| 6,103,267 A | * 8/2000 | Mitchnick et al. | 424/489 |

\* cited by examiner

*Primary Examiner*—Raymond Henley, III
*Assistant Examiner*—Donna Jagoe

(57) ABSTRACT

There is provided an emulsion having a substantially non-aqueous phase, a substantially aqueous phase, a vitamin C component and a pigment. Such an emulsion is both cosmetically and aesthetically acceptable.

36 Claims, No Drawings

PIGMENTED VITAMIN C COMPOSITION

RELATED APPLICATIONS

This application is a continuation-in-part of application Ser. No. 09/150,806, now U.S. Pat. No. 6,299,889 filed Sep. 10, 1998.

BACKGROUND OF THE INVENTION

1. Field of the Invention

The present invention relates generally to compositions for topical application and, particularly, to pigmented compositions for application to the skin. More particularly, the present invention relates to a pigmented vitamin C composition.

2. Description of the Prior Art

Ascorbic acid, also known as vitamin C, has long been recognized as a substance benefiting the skin. However, ascorbic acid has also long been recognized as unstable. For example, although ascorbic acid is readily soluble in water, rapid oxidation occurs in substantially aqueous media. In addition, the solubility of ascorbic acid in anhydrous media has been reported to be relatively poor. Moreover, ascorbic acid is sensitive to the influence of light and oxygen.

The instability of ascorbic acid runs counter to the effectiveness that is sought. Furthermore, it can be a source of unpleasantness for the user. For example, the instability of the active substance may lead to color and/or odor changes in the composition containing it.

Heretofore, one way of dealing with the instability of ascorbic acid is stabilizing it in an acidic medium. However, cosmetic compositions that stabilize ascorbic acid in an acidic medium invite a different set of problems. For example, the incorporation of a pigment into such an acidic medium becomes very difficult.

A pigment is a water-insoluble dye that may be used in cosmetic compositions. Pigments have several beneficial characteristics when used in cosmetic compositions. For example, pigments are inexpensive, provide ultraviolet light protection, and produce vibrant colors. However, pigments hydrolyze under acidic conditions. Hydrolysis leads to the breakdown and discoloration of the pigments. Accordingly, the cosmetic composition discolors.

Thus, there is a need for a cosmetic composition that stabilizes ascorbic acid and also incorporates a pigment.

SUMMARY OF THE INVENTION

It is an object of the present invention to provide a cosmetic composition having a vitamin, C component and a pigment.

It is another object of the present invention to provide such a composition that stabilizes both the vitamin C component and the pigment.

It is still another object of the present invention to provide such a composition that is cosmetically and aesthetically acceptable.

It has been unexpectedly discovered that a vitamin C component may be stabilized in a substantially aqueous phase of an emulsion that has a pigment in a substantially non-aqueous phase. Such an emulsion is both cosmetically and aesthetically acceptable.

DETAILED DESCRIPTION OF THE INVENTION

The present invention is a composition having a vitamin C component in an emulsion. The phrase "vitamin C component," as used herein, means vitamin C, and its derivatives and mixtures thereof.

The present invention is an emulsion having a substantially aqueous phase and a substantially non-aqueous phase. It has been unexpectedly discovered that such an emulsion may effectively sequester and, thus, stabilize both a vitamin C component and a pigment. The vitamin C component is substantially or, more preferably, completely sequestered and stabilized within the substantially aqueous phase. The pigment is substantially or, more preferably, completely sequestered within the substantially non-aqueous phase and, thus, from the aqueous phase.

The substantially aqueous phase is about 5 percent by weight (wt. %) to about 75 wt. % of the total weight of the composition. More preferably, the substantially aqueous phase is about 20 wt. % to about 50 wt. %, and most preferably about 30 wt. % to about 50 wt. % of the total weight of the composition.

The vitamin C component is dispersed in the substantially aqueous phase of the present invention. The vitamin C component is preferably present in an amount about 0.04 wt. % to about 20 wt. % of the total weight of the composition. More preferably, the vitamin C component is about 0.05 wt. % to about 7 wt. %, and most preferably about 0.075 wt. % to about 5 wt. %, of the total weight of the composition. Preferably, the vitamin C component includes vitamin C (ascorbic acid). More preferably, the vitamin C component is vitamin C.

The present invention can utilize the vitamin C preparations disclosed in and commonly assigned U.S. patent application Ser. No. 09/150,806, filed on Sept. 10, 1998, now U.S. Pat. No. 6,299,889 for "Stable Ascorbic Acid Preparation for Topical Use," the entirety of which is incorporated herein by reference.

One example of such a vitamin C preparation includes about 0.1 to about 16 wt. % ascorbic acid, about 20 to about 85 wt. % polyhydric alcohol, about 0.3 to about 25 wt. % organic carbonate, about 0.1 to about 12 wt. % water, and optionally, about 5 to about 38 wt. % monohydric alcohol, and about 0.01 to about 3 wt. % hydroxyalkyl cellulose. More preferably, an example of such a vitamin C preparation has about 8 wt. % to about 10 wt. % ascorbic acid, about 25 wt. % to about 35 wt. % monohydric alcohol, about 35 wt. % to about 45 wt. % polyhydric alcohol, about 0.1 wt. % to about 1 wt. % hydroxyalkyl cellulose, about 1 wt. % to about 10 wt. % organic carbonate, and about 8 wt. % to about 12 wt. % water.

The substantially non-aqueous phase of the present invention has a substantially anhydrous base. The substantially anhydrous base is preferably a cosmetically acceptable fluid, gel, wax, or gum. The anhydrous base may include one or more of: (1) silicones, such as cyclomethicone, dimethicone, dimethicone copolyol, cetyl dimethicone copolyol, dimethiconol, phenyl trimethicone, stearoxytrimethylsilane, or mixtures thereof; (2) mineral and vegetable oils, such as mineral oil, safflower oil, castor oil, or mixtures thereof; and (3) hydrocarbon esters, such as octyl palmitate, proplyene glycol dicaprylate/dicaprate, isopropyl palmitate, or mixtures thereof. Additional examples of silicones include, but are not limited to, silicone gels (non-limiting examples of which include cyclomethicone/quaternium-18 hectorite/propylene carbonate (75/25/5)) and silicone compatible wax (a non-limiting example of which is trimethyl/stearoxy polysiloxane).

The substantially non-aqueous phase is about 5 wt. % to about 70 wt. % of the total weight of the composition. More preferably, the non-aqueous phase is about 20 wt. % to about 60 wt. %, and most preferably about 20 wt. % to about 40 wt. % of the total weight of the composition.

The pigment is dispersed in the substantially non-aqueous phase. The pigment may be, for example, titanium dioxide, iron oxide, mica, ultramarine, manganese violet, zinc oxide, bismuth oxychloride, ferric ammonium ferrocyanide, ferric ferrocyanide, chromium hydroxide green, or any mixture thereof. Preferably, the pigment is a metal oxide, such as titanium dioxide, iron oxide, or zinc oxide. Moreover, the present invention may also include any FD&C or D&C approved colorant and any derivatives or lakes of such colorants.

Although the pigment may be coated or uncoated, it is preferred that the pigment is coated. Examples of substances that may be used to coat the pigment include, but are not limited to, fluorosilane, alkyl silane, perfluoropolymethylisopropyl ether, lauryl lysine, magnesium myristate, polyethylene, phospholipids, dimethicone, lecithin, or any mixture thereof.

The pigment is preferably present in an amount about 0.01 wt. % to about 20 wt. % of the total weight of the composition. More preferably, the pigment is present in an amount about 1 wt. % to about 15 wt. %, and most preferably about 5 wt. % to about 10 wt. % of the total weight of the composition.

A composition according to the present invention may also include a secondary active agent. The purpose of adding a secondary active agent is to enhance or augment the aesthetic improvement to the skin achieved by the vitamin C component. The substances that may be used as the secondary active agent include, but are not limited to, one or more ultraviolet (UV) light radiation protection agents (i.e., absorbers and/or blockers), exfoliating agents, botanical extracts, wrinkle reducing agents, wrinkle preventing agents, anti-acne agents, and hypopigmenting agents. Preferred hypopigmenting agents are arbutin and licorice extract.

The secondary active ingredient is added to the phase with which it is most compatible prior to forming the emulsion. For example, when the secondary active agent is a water-insoluble UV light radiation protection agent, it is added to the non-aqueous phase prior to forming the emulsion. Similarly, a water-soluble secondary active ingredient is added to the aqueous phase prior to forming the emulsion.

When the present invention is used as a skin-lightening composition, one or more UV light radiation protection agents, oxa acids, oxa diacids, or combinations thereof are preferably used as the secondary active agent. The addition of a UV light radiation protection agent compensates for the increased photosensitivity of the skin. Titanium dioxide, avobenzone and cinnamate derivatives, such as octyl methoxycinnamate, are preferred UV light radiation protection agents. Preferably, the UV light radiation protection agent protects against both UV-A and UV-B light.

When used, the UV light radiation protection agent is present in an amount about 2 wt. % to about 25 wt. % of the total weight of the composition. More preferably, the UV light radiation protection agent is present in an amount about 2 wt. % to about 20 wt. %, and most preferably about 2 wt. % to about 10 wt. % of the total weight of the composition.

Acids may be added to the substantially aqueous phase of the present invention to enhance the beneficial effects achieved by the vitamin C component. Such optional acids include one or more oxa acids, oxa diacids, as well as alpha-hydroxy and beta-hydroxy acids. Such acids also promote skin exfoliation.

Oxa acids and oxa diacids are disclosed in commonly assigned U.S. Pat. Nos. 5,847,003 and 5,847,513, respectively, both of which are herein incorporated in their entireties by reference. Preferably, when the acid is the oxa acid, it is preferred that the acid comprises 3,6,9-trioxaundecatedioic acid. When the acid is an alpha-hydroxy acid, it is preferred that the alpha-hydroxy acid includes glycolic acid, lactic acid, malic acid, tartaric acid, or any mixture thereof. More preferably, the alpha-hydroxy acid includes glycolic, lactic, or a mixture thereof.

When used, the acid is present from about 0.01 wt. % to about 20 wt. % of the total weight of the composition. More preferably, the acid may be about 0.01 wt. % to about 10 wt. %, and most preferably about 0.01 wt. % to about 6 wt. % of the total weight of the composition.

A composition according to the present invention may optionally include many other ingredients known to the art. Such optional ingredients include one or more fragrances, preservatives, fillers, emulsifying agents, antioxidants, surfactants, chelating agents, gelling agents, emollients, moisturizers, vitamins, minerals, viscosity builders, and fillers. Examples of emulsifiers include, but are not limited to, cyclomethicone/dimethicone copolyol (90/10), cetyl dimethicone copolyol, sorbitan sesquloleate, and mixtures thereof.

The optional ingredients may be present in an amount from about 1 wt. % to about 60 wt. %. More preferably, the optional ingredients may be present in an amount from about 1 wt. % to about 50 wt. %, and most preferably from about 5 wt. % to about 50 wt. %.

According to the present invention, a preferred emulsion includes: (1) about 0.1 wt. % to about 6 wt. % vitamin C component; (2) about 6.0 wt. % to about 19.0 wt. % of at least one emulsifier; (3) about 4.5 wt. % to about 19.0 wt. % of one or more silicone fluids; (4) about 3 wt. % to about 10 wt. % of one or more silicone gels; (5) about 0.5 wt. % to about 10 wt. %, more preferably from about 1 wt. % to about 5 wt. %, of one or more silicone compatible waxes; (6) about 0.1 wt. % to about 0.6 wt. % of one or more viscosity builders; and (7) water. An example of a viscosity builder is xanthan gum.

A preferred method for making the present invention has the following steps:

(1) Form an acidic, substantially aqueous phase by adding together the water-soluble optional ingredient(s) and secondary agent(s). This substantially aqueous phase will preferably be the internal phase of a water-in-oil emulsion. Optionally, a basic ingredient, such as ammonium hydroxide, may used to adjust the pH of the acidic, substantially aqueous phase. The pH of the acidic, substantially aqueous phase is about 2 to about 6.9, more preferably about 2.5 to about 6.5, or most preferably about 3 to about 5.

(2) Form a substantially non-aqueous phase by grinding an uncoated or coated pigment and other water-insoluble ingredient(s), such as octyl methoxycinnimate, into a substantially anhydrous base. This non-aqueous phase will preferably be the external phase of the water-in-oil emulsion. The grinding is preferably done under high speed with homogenization.

(3) Combine the acidic, substantially aqueous phase and the substantially non-aqueous phase at a temperature range of about 35° C. to about 65° C., more preferably about 45° C. to about 55° C., with light homogenization to form an emulsion.

(4) Add the vitamin C preparation including the Vitamin C component to the emulsion.

Optionally, the vitamin C preparation may be added to the acidic, substantially aqueous phase prior to emulsification.

A composition having the vitamin C component and the pigment that is formulated according to the present invention will effectively stabilize the vitamin C component within the acidic, substantially aqueous phase, while simultaneously segregating the pigment in the substantially non-aqueous phase from the aqueous phase. Thus, the efficacy of the vitamin C component is maintained, the pigment is also substantially prevented from hydrolyzing, and the composition is able to maintain its aesthetic appearance over time.

Vitamin C components have many known biological functions. In general, the composition has a vitamin C component both as an antioxidant and to obtain a degree of skin lightening. Nonetheless, the present invention is useful for any skin condition that may be treated with, or prevented by, the application of a vitamin C component. For example, the formulations of the present invention may be used for stimulating collagen synthesis, protecting against ultraviolet radiation and pollution, depigmenting the skin, neutralizing free radicals, compensating for vitamin E deficiency, and treating and preventing wrinkles. Broadly, the present invention may be used to improve the overall aesthetic appearance of skin. Examples of such improvements include, but are not limited to, improvements in skin clarity, evenness of skin tone and improvements in skin texture.

The present invention is topically applied as a cosmetic or skin-care composition. The present invention may be incorporated into suitable cosmetic/skin care vehicles, such as creams, serums, lotions, sticks or topical patches. The present invention can be in the form of a foundation, a beauty-mask, a moisturizer, an eyeshadow, a lipstick; as well as other cosmetic and skin care composition forms.

The present invention having been described with particular reference to the preferred forms thereof, it will be obvious that various changes and modifications may be made herein without departing from the spirit and scope of the invention as defined in the appended claims.

We claim:

1. A topical composition comprising:
   an emulsion having a substantially aqueous phase with a vitamin C preparation and a substantially non-aqueous phase with a pigment, wherein the vitamin C preparation has about 0.3 to about 25 wt % organic carbonate and about 0.1 to about 16 wt % of a vitamin C Component based on the total weight of the vitamin C preparation.

2. The composition of claim 1, wherein the composition comprises vitamin C in an amount about 0.04 wt % to about 20 wt % based on the total weight of the composition.

3. The composition of claim 1, wherein said vitamin C component is substantially sequestered in said substantially aqueous phase.

4. The composition of claim 1, wherein said pigment is selected from the group consisting of: titanium dioxide, iron oxide, mica, ultramarine, manganese violet, zinc oxide, bismuth oxychloride, ferric ammonium ferrocyanide, ferric ferrocyanide, chromium hydroxide green, FD&C colorant, derivative of FD&C colorant, lake of FD&C colorant, D&C colorant, derivative of D&C colorant, lake of D&C colorant, and mixtures thereof.

5. The composition of claim 1, wherein said pigment is coated with a substance selected from the group consisting of fluorosilane, alkyl silane, perfluoropolymethylisopropyl ether, lauryl lysine, magnesium myristate, polyethylene, phospholipids, dimethicone, lecithin, and mixtures thereof.

6. The composition of claim 5, wherein said pigment is coated with said fluorosilane.

7. The composition of claim 1, further comprising a secondary active agent.

8. The composition of claim 7, wherein said secondary active agent is an acid selected from the group consisting of oxa acid, oxa diacid, alpha-hydroxy acid, beta-hydroxy acid, and any mixture thereof.

9. The composition of claim 8, wherein said acid is present at about 0.01 wt. % to about 20 wt. % of the total weight of the composition.

10. The composition of claim 1, further comprising an optional ingredient selected from the group consisting of: fragrances, preservatives, fillers, emulsifying agents, antioxidants, surfactants, chelating agents, gelling agents, emollients, moisturizers, vitamins, minerals, viscosity builders, fillers, and mixtures thereof.

11. The composition of claim 1, further comprising an ultraviolet light radiation protection agent.

12. The composition of claim 11, wherein said ultraviolet light radiation is dispersed in the substantially non-aqueous phase.

13. The composition of claim 11, wherein said ultraviolet light radiation protection agent is present at about 2 wt. % to about 25 wt. % of the total weight of the composition.

14. The composition of claim 11, wherein said ultraviolet light radiation protection agent is avobenzone.

15. The composition of claim 1, wherein said substantially non-aqueous phase is present at about 5 wt. % to about 70 wt. % of the total weight of the composition.

16. The composition of claim 1, wherein the substantially non-aqueous phase comprises a substantially anhydrous base selected from the group consisting of silicone, mineral oil, vegetable oil, hydrocarbon ester, and mixtures thereof.

17. The composition of claim 1, wherein the substantially non-aqueous phase comprises a substantially anhydrous base selected from the group consisting of cyclomethicone, dimethicone, dimethicone copolyol, cetyl dimethicone copolyol, dimethiconol, phenyl trimethicone, stearoxytrimethylsilane, mineral oil, safflower oil, castor oil, octyl palmitate, proplyene glycol dicaprylate/dicaprate, isopropyl palmitate, and any mixtures thereof.

18. A method of preparing the composition of claim 1, comprising:
   forming said emulsion; and
   adding a vitamin C component to said emulsion.

19. The method of claim 18, wherein said emulsion includes at least one secondary active agent selected from the group consisting of an acid, an ultraviolet light radiation protection agent, and a mixture thereof.

20. The method of claim 18, wherein the emulsion is water-in-oil.

21. The composition of claim 1, wherein said pigment is substantially sequestered in said substantially non-aqueous phase.

22. The composition of claim 1, wherein said pigment is selected from the group consisting of iron oxide, mica, ultramarine, manganese violet, bismuth oxychloride, ferric ammonium ferrocyanide, ferric ferrocyanide, chromium hydroxide green, FD&C colorant, derivative of FD&C colorant, lake of FD&C colorant, D&C colorant, derivative of D&C colorant, lake of D&C colorant, and any combinations thereof.

23. The topical composition of claim 1, wherein the emulsion is water-in-oil.

24. The composition of claim 1, wherein the composition comprises vitamin C in an amount about 0.05 wt % to about 7 wt % based on the total weight of the composition.

25. The composition of claim 1, wherein the composition comprises vitamin C in an amount about 0.075 wt % to about 5 wt % based on the total weight of the composition.

26. An emulsion for topical application comprising:
   an acidic, substantially aqueous internal phase having about 0.04 wt % to about 20 wt % of a vitamin C component and an organic carbonate; and
   a substantially non-aqueous external phase having a pigment.

27. The emulsion of claim 26, wherein said substantially non-aqueous external phase includes an anhydrous base with a substance selected from the group consisting of silicone fluid, silicone gel, silicone compatible wax, and mixtures thereof.

28. The emulsion of claim 26, wherein the emulsion is water-in-oil.

29. A method of preparing the emulsion of claim 26, comprising:
   forming said emulsion; and
   adding a vitamin C component to said emulsion.

30. A topical composition comprising an emulsion having a substantially aqueous phase and a substantially non-aqueous phase, the emulsion having about 0.1 wt. % to about 6 wt. % vitamin C component, about 6.0 wt. % to about 19.0 wt. % of at least one emulsifier, about 4.5 wt. % to about 19.0 wt. % of one or more silicone fluids, about 3 wt. % to about 10 wt. % of one or more silicone gels, about 0.5 wt. % to about 10 wt. % of one or more silicone compatible waxes, about 0.1 wt. % to about 0.6 wt. % of one or more viscosity builders, and about 0.01 wt. % to about 20 wt. % of a pigment, the pigment being present in the substantially non-aqueous phase.

31. The topical composition of claim 30, wherein the emulsion is water-in-oil.

32. An emulsion for topical application, comprising:
   a pigment; and
   a vitamin C preparation, said vitamin C preparation having a vitamin C component at about 0.1 to about 16 wt % and an organic carbonate at about 0.3 to about 25 wt % based on the total weight of the vitamin C preparation.

33. The composition of claim 32, wherein said vitamin C preparation has a polyhydric alcohol.

34. The composition of claim 33, wherein said vitamin C preparation has water.

35. The composition of claim 32, wherein said pigment is selected from the group consisting of titanium dioxide, zinc oxide, iron oxide, mica, ultramarine, manganese violet, bismuth oxychloride, ferric ammonium ferrocyanide, ferric ferrocyanide, chromium hydroxide green, FD&C colorant, derivative of FD&C colorant, lake of FD&C colorant, D&C colorant, derivative of D&C colorant, lake of D&C colorant, and any combinations thereof.

36. The emulsion of claim 32, wherein the emulsion is water-in-oil.

\* \* \* \* \*